(12) United States Patent
Koch et al.

(10) Patent No.: US 6,756,052 B1
(45) Date of Patent: Jun. 29, 2004

(54) DEVICE AND METHOD FOR INCREASING THE TRANSDERMAL PERMEATION OF MEDICAMENTS

(75) Inventors: Andreas Koch, Melsbach (DE); Christian von Falkenhausen, Meckenheim (DE); Rudolf Matusch, Marburg (DE); Bernd Adam, Treysa (DE)

(73) Assignee: LTS Lohmann Therapie-Systeme AG, Andernach (DE)

( * ) Notice: Subject to any disclaimer, the term of this patent is extended or adjusted under 35 U.S.C. 154(b) by 0 days.

(21) Appl. No.: 09/979,251

(22) PCT Filed: May 17, 2000

(86) PCT No.: PCT/EP00/04460

§ 371 (c)(1),
(2), (4) Date: Nov. 19, 2001

(87) PCT Pub. No.: WO00/71100

PCT Pub. Date: Nov. 30, 2000

(30) Foreign Application Priority Data

May 21, 1999 (DE) .......................................... 199 23 427

(51) Int. Cl.⁷ .......................... A61F 13/02; A61L 15/16
(52) U.S. Cl. ....................... 424/448; 424/447; 424/449; 514/947
(58) Field of Search ................................ 424/449, 448; 514/947, 946

(56) References Cited

U.S. PATENT DOCUMENTS

| | | | |
|---|---|---|---|
| 4,557,934 A | | 12/1985 | Cooper |
| 4,599,342 A | | 7/1986 | LaHann |
| 4,685,911 A | | 8/1987 | Konno et al. |
| 4,767,402 A | | 8/1988 | Kost et al. |
| 4,830,855 A | | 5/1989 | Stewart |
| 4,849,224 A | * | 7/1989 | Chang et al. ................. 424/434 |
| 4,931,283 A | * | 6/1990 | Tsuk ............................ 424/49 |
| 4,956,171 A | * | 9/1990 | Chang ........................ 424/449 |
| 4,959,054 A | | 9/1990 | Heimke et al. |
| 4,963,360 A | | 10/1990 | Argaud |
| 4,990,340 A | * | 2/1991 | Hidaka et al. ............... 424/449 |
| 5,135,479 A | | 8/1992 | Sibalis et al. |
| 5,306,503 A | | 4/1994 | Müller et al. |
| 5,538,736 A | * | 7/1996 | Hoffmann et al. .......... 424/448 |
| 5,733,255 A | | 3/1998 | Dinh et al. |
| 5,737,774 A | | 4/1998 | Petty-Saphon et al. |
| 5,750,141 A | | 5/1998 | Roberts et al. |
| 5,811,465 A | | 9/1998 | Huntington et al. |
| 5,853,751 A | | 12/1998 | Masiz |
| 5,902,601 A | | 5/1999 | Horstmann |
| 5,976,547 A | * | 11/1999 | Archer et al. ............. 424/195.1 |
| 6,190,689 B1 | | 2/2001 | Hoffmann et al. |
| 6,217,852 B1 | * | 4/2001 | Gildenberg et al. ........... 424/59 |

FOREIGN PATENT DOCUMENTS

| | | |
|---|---|---|
| CA | 1336665 | 8/1995 |
| CA | 2106374 | 3/1997 |
| CA | 2302601 | 3/1999 |
| DE | 35 25 741 | 1/1987 |
| DE | 37 14 140 | 11/1988 |
| DE | 39 02 981 | 8/1989 |
| DE | 38 09 978 | 10/1989 |
| DE | 41 10 027 | 10/1992 |
| DE | 36 33 487 | 4/1994 |
| DE | 43 32 094 | 3/1995 |
| DE | 44 16 927 | 8/1995 |
| DE | 196 50 471 | 6/1998 |
| DE | 197 38 855 | 3/1999 |
| EP | 0 153 200 | 8/1985 |
| EP | 0 464 573 | 1/1992 |
| GB | 2 152 815 | 8/1985 |
| GB | 2 215 208 | 9/1989 |
| WO | WO 90/09809 | 9/1990 |
| WO | 97/13482 | 4/1997 |

* cited by examiner

Primary Examiner—Carlos A. Azpuru
Assistant Examiner—Micah-Paul Young
(74) Attorney, Agent, or Firm—Frommer Lawrence & Haug LLP

(57) ABSTRACT

The invention relates to a device and a method for increasing the transdermal permeation of medications. The invention is characterized in that a constituent which effects a local increase in temperature and/or an increase in blood flow or the skin is administered in a addition to the transdermally applied active substance.

12 Claims, 2 Drawing Sheets

DEVICE AND METHOD FOR INCREASING THE TRANSDERMAL PERMEATION OF MEDICAMENTS

The invention relates to a device for and to a method of increasing the dermal and/or transdermal permeation of drugs.

The transdermal administration of pharmaceutical active substances has been known from the time of the first commercial use of a scopolamine transdermal therapeutic system (Scopoderm TTS). Other active substances (nitroglycerine, estradiol, clonidine, isosorbide dinitrate, fentanyl, nicotine, norethisterone etc.) as well are now offered in the form of such a TTS. These active substance patches are adhered to the skin of a patient. The active substance is then released in a controlled manner from the TTS to the skin of the patient, travels through the various layers of the skin, and, finally, enters the circulation.

A problem with this mode of administration of a substance having a systemic action is very frequently that the path taken by the active substance through the differently constructed layers of the skin is very long and the transport of the active substance until it enters the circulation is time-consuming. There are a number of reasons for this. First, the skin possesses a natural barrier function against the penetration of foreign substances into the body.

Secondly, substances having a very large molecular radius possess only a low diffusion coefficient. The latter is a measure of the ability of a substance to travel within a medium; in the case in hand, therefore, the permeation behavior within the skin layers. And, finally, physicochemical interactions (for example, polar interactions, dipole-dipole interactions, etc.) between the active substance and the various constituents of the different skin layers may lower the rate of diffusion of an active substance in the skin.

All of these phenomena may result in the percutaneous and subsequent absorption of the active substance taking place so slowly that a pharmacological effect occurs only with considerable time delay. This period between the application of a TTS to the skin of the patient and the onset of the pharmacological effect is referred to by the skilled worker as the lag time.

Almost logically, therefore, enhancing the percutaneous permeation of a transdermally administerable active substance has been the subject of extensive research work, especially by the pharmaceutical industry. It has led to the use of a very wide variety of substances which improve skin penetration (known as enhancers) and to the development of specific substances, e.g., Azone®. Enhancers include alcohols, amides, amino acids, derivatives of Azone®, essential oils, fatty acids and fatty acid derivatives such as fatty acid esters, macrocyclic compounds, phospholipids, pyrrolidones, sulfoxides, and others.

When such enhancers are given, the increase in skin penetration (or, more precisely, the acceleration of an active substance's entry into and travel through the various skin layers and thus, ultimately, the raising of the transdermal absorption rate as well) is essentially achieved by virtue of the fact that these enhancers penetrate the uppermost layers of the skin, where they alter the structure of the skin in such a way that its barrier function is no longer fully effective. This mode of action is explained at the molecular level as follows: the enhancers incorporate themselves into biological membranes and alter the natural structure of lipids and proteins—causing them, for example, to swell. The active substance applied to the skin is then able to travel more easily, i.e., more quickly, through the different layers of the skin.

The use of the prior art enhancers, however, also possesses many disadvantages. First of all, the enhancer must not be toxic and must not cause any physiological side effects. Further, there must be no chemical or physical incompatibilities between enhancer and both the active substance and the other materials constituting the TTS. Finally, the enhancer must be present in the TTS in an amount such that the permeation-intensifying effect is retained over the entire period of its application (generally from 16 to 24 hours, although there are also 3-day plasters already available). An inevitable result of this, however, is often that said enhancer is administered to the patient likewise in amounts such as to cause a systemic effect.

It is an object of the present invention to accelerate the penetration of an active substance into the skin and/or the travel of this active substance through the different layers of the skin and/or the transport of this active substance through the blood capillary system of the dermis and/or the blood vessels of the hypodermis in such a way that absorption through the skin takes place more rapidly and thus a reduction in the lag time is achieved. In particular, practical transdermal application should be made accessible to active substances which by their nature exhibit a long lag time for absorption through the skin.

This object is achieved by a device which comprises a component which brings about a local temperature increase in the skin and/or increases the circulation. The device of the invention can be, for example, an ointment, a solution, a suspension, an emulsion, a foam, a paste, a gel or a patch, a patch of this kind being a preferred embodiment.

The invention further provides a method which comprises achieving an increase in the rate of penetration of an active substance into the skin and/or of travel of this active substance through the different layers of the skin and/or of transport of this active substance through the blood capillary system of the dermis and/or the blood vessels of the hypodermis by means of a local temperature increase and/or an increase in the circulation of the skin. In this way, ultimately, the transdermal absorption rate of said active substance is increased and the lag time to the onset of a pharmacological effect of said active substance is reduced.

The use of substances which bring about a local temperature increase in the skin for the purpose of increasing the rate of penetration of an active substance into the skin and/or of travel of this active substance through the different layers of the skin and/or of transport of this active substance through the blood capillary system of the dermis and/or the blood vessels of the hypodermis is likewise provided by the present invention. It is possible to achieve either a short-term effect (that is, up to the onset of the pharmacological effect) or a long-term effect (that is, throughout the duration of transdermal administration of the active substance in question).

Further elucidation of the invention is aided by the following definitions:

Skin refers to the uninjured, i.e., undamaged, unshaved skin of a mammal, especially that of a human, said skin having its normal hair cover. For the purposes of this invention, the term skin does not include mucous membrane. Normal skin consists essentially of three layers: the epidermis (situated externally), the dermis, and the hypodermis (which is situated below). The hypodermis is also referred to as the subcutis. The epidermis in turn is composed of the stratum corneum, stratum lucidum, stratum granulosum, stratum spinosum and stratum germativum. The dermis contains, inter alia, the blood capillary system. The hypodermis houses the blood vessels.

Penetration refers to the penetration of an active substance into the outer layers of the skin, especially into those of the epidermis. Permeation refers to the travel of the active substance through the skin, especially through the epidermis (including the stratum corneum) and the dermis.

The term dermal administration as used in the present description means that an active substance is applied to the skin and develops a local or regional (i.e., topical) action in the epidermis and/or dermis. Transdermal administration in the present description means that an active substance is applied to the skin, passes through the epidermis and/or dermis into the blood stream or into the lymph system, is distributed from there throughout the body, and develops a systemic action at the target site. Transdermal absorption is used to denote the takeup of an active substance by the under-skin blood vessels following transdermal administration, thereby permitting a systemic action of the active substance taken up.

Active substances for the purposes of the present invention are essentially pharmaceutical and/or cosmetic active substances which serve to prevent, alleviate, heal or reveal disorders. They include substances which are able to exert a topical and/or systemic action. Active substances are known to the skilled worker and can be found in standard works, such as, for example, the German "Red List" (pharmaceutical active substances) and "Green List" (cosmetic active substances). Further active substances are specified in U.S. Pat. No. 4,557,934 and in the sources cited therein (col. 10, lines 18–35). In order to avoid repetition, the content of that patent insofar as it refers to active substances is considered part of the disclosure of the present invention by reference. In principle, the nature of the active substance is not critical to the present invention. The term active substance should therefore not be interpreted in a manner which restricts the subject matter of the invention.

Active substances which by their nature exhibit a long lag time on absorption through the skin include the following: opiates such as, for example, morphine, diamorphine, buprenorphine; fentanyl, estrogens such as, for example, 17β-estradiol; hormones such as, for example, testosterone, norethisterone, gestagens; peptides such as, for example, insulin;

analgesics; and alkaloids. This type of systemic active substance can be made amenable to transdermal administration in a particularly advantageous way by means of the-subject matter of the invention.

The component which brings about a local temperature increase and/or an increase in the circulation of the skin is a substance or substance mixture which when applied to the skin results in local heating of the skin. Such substances include especially rubefacientia, vasodilators, and hyperemic substances.

Rubefacientia are substances which as a consequence of hyperemia have a skin irritant and/or skin reddening action. Rubefacientia are therefore a particular group of hyperemic substances. They include, for example, pelargonic acid vanillyl amide, cayenne pepper oil resin, capsicum extract, capsicum tincture, cayenne pepper extract, cayenne pepper, and capsaicin.

Vasodilators are vessel widening substances which bring about a widening of the blood vessels by, for example, relaxing the vessel musculature. This is often accompanied by a lowering of blood pressure. This also takes place, of course, in the peripheral blood vessels, so producing increased blood flow through the area affected. Vasodilators include nicotinic acid; derivatives of nicotinic acid such as, for example, nicotinyl alcohol, benzyl nicotinate, nicotinamide, etc.; adenosine compounds; xanthine, derivatives of xanthine such as caffeine, etc.; arnica extract, arnica blossom extract, pyridyl-3-carbinol and its salts, camomile, phytolacca, guaia gum, cinnabaris, creosotum, Luffa operculata, and tincture of Rhus toxicodendron.

Hyperemic substances are substances which increase circulation. The increase in circulation is brought about by increased blood afflux (reactive hyperemia) or reduced blood efflux (restriction hyperemia). This can have various causes. Hyperemic substances include essential oils, menthol, camphor, nicotinic esters, salicylic esters, hydroxyethyl salicylate, methyl salicylate, and ortho-carbamoylphenoxyacetic acid.

The heat effect in the skin is, therefore, brought about essentially by an improvement in the circulation to the peripheral blood vessels (capillary system). It is not based on a heat effect in the form, for example, of thermal conduction, ultrasound, thermal radiation, etc., being exerted on the skin from the outside. There is no transport of energy from an external energy source into the skin.

Devices of the abovementioned kind are produced in a known manner where the device in question is an ointment, solution, suspension, emulsion, foam, paste, aerosol, or gel. All that must be done is to incorporate the component which brings about a local temperature increase in the skin into the active substance composition in an appropriate process step. Said ointment, solution, suspension, emulsion, foam, paste, aerosol or gel can be applied to the skin area in question directly prior to application of the active substance ITTS. It can also be applied to the skin around the TTS following application of the latter.

Owing to the difficulty in controlling the amount applied in this case of the component which brings about a local temperature increase of the skin, and owing to any concomitant adhesion problems of the TTS on the skin, the preferred embodiment is, as stated, a patch.

A patch of this kind, i.e., a dermal or transdermal therapeutic system, can comprise the following structural elements: an active substance impermeable backing layer, an active substance reservoir, an active substance release controlling (semipermeable or microporous) membrane, an adhesive layer containing active substance, and a redetachable protective layer (known as the release liner).

In accordance with the invention, the component which brings about a local temperature increase and/or circulation increase in the skin can be present in the active substance reservoir and/or in the adhesive layer containing active substance. Alternatively, in order to avoid incompatibilities but also as a preferred embodiment, the component which brings about a local temperature increase of the skin can also be present in a structural element of the device which is spatially separate from the structural elements containing active substance.

The simplest embodiment of this case is a pressure sensitive adhesive layer which comprises the component that brings about a local temperature increase and/or increase in circulation in the skin and which is equipped with a backing layer impermeable to said component. In this embodiment, the device consists of two separate devices, namely an active substance release device and the device containing the component which brings about a local temperature increase and/or circulation increase in the skin. The active substance release device, an active substance TTS for example, is applied first of all to the skin of the patient. Then the device containing the component which brings about a local temperature increase of the skin is placed atop it and judicially fixed—for example, by means of a pressure sensitive adhesive layer located on the bottom, pressure sensitive adhesive strips located on the edge of the device, or a further, cover patch. Likewise preferred is an embodiment in which an outer segment containing the component which brings about a local temperature increase and/or circulation increase in the skin is disposed around an inner segment which contains the active substance intended for transdermal administration. The form of the inner segment is in principle not critical; it can be circular, rectangular or square. The form of the outer segment is likewise in principle not critical; it can also be circular, rectangular or square. Alternatively, the outer segment can be disposed around the inner segment in the form of a ring or as two or more sections which are, for example, rectangular or semicircular. This embodiment is particularly suitable since it profits from the formation of a horizontal concentration gradient in the epidermis and in the dermis/subcutis. Although this so-called lateral diffusion can be derived from the structure of the stratum corneum with its lamellar lipid-water bilayers, this phenomenon has, surprisingly, to date not been considered by those skilled in the art for a practical implementation in terms of increasing the rate of penetration into the skin and/or of travel through the skin, in particular for increasing the transdermal absorption rate of an active substance applied to the skin.

In this advantageous embodiment, the outer segment overhangs the inner segment to a considerable extent; for example, by several millimeters (e.g.: from 5 to 25) or by the length of the diameter of the inner segment. In this way, the principle responsible for the increase in the transdermal absorption rate of the active substance acts on an area which projects beyond the mere release area of the transdermally administered active substance.

The area of the pressure sensitive adhesive layer, or of the outer segment, which contains the component which brings about a local temperature increase and/or increase in the circulation of the skin is generally smaller than 100 cm$^2$.

A preferred embodiment of this kind can likewise be produced by processes known to the skilled worker, as described, for example, in DE 37 14 140, DE 38 09 978 and DE 41 10 027. In order to avoid repetition, the relevant section of the disclosure contents of these documents has not been reproduced here but is considered to be incorporated by reference. It is clear that when producing the outer segment the component which brings about a local temperature increase of the skin must be incorporated into the matrix forming the outer segment, in the appropriate working step. The spatial separation of the segments containing the component which brings about a local temperature increase and/or circulation increase in the skin from the segments containing the active substance intended for transdermal administration is achieved by horizontal or vertical barrier layers or material voids.

Depending on the amount of the component which brings about a local temperature increase and/or circulation increase in the skin, the action of the device of the invention may extend over a relatively long period: for example, about 8, 16, 24, 48 or even 72 hours. The device of the invention is applied to the skin of the patient under normal conditions, i.e., at normal—that is, not increased—external skin temperature. Alternatively, the device of the invention can be applied before and during an iontophoresis treatment.

Within the device, the amount of the substance which is able to bring about a local temperature increase and/or circulation increase in the skin depends on whether the desire is for a short-term effect, until the onset of the pharmacological effect, or a long-term effect, throughout the duration of the transdermal administration of the active substance in question.

It is also guided in each specific case by the specific properties of the substance. In general, therefore, the amount of this substance within the device is between 0.5 and 20% by weight.

The device of the invention is preferably free from permeation enhancers, i.e., substances which by intervening in the structure of the skin achieve an improvement in the skin permeation of a dermally administered active substance, but may, if desired, comprise such substances. A list of these substances can be found from the article by D. W. Osborne and J. J. Hill on "Skin penetration enhancers cited in the technical literature" on the Internet website http://pharmtech.com/technical/osborne/osborne.htm.

The examples which follow serve to elucidate the mode of action of the invention.

EXAMPLE 1

Three samples of a commercially available estradiol active substance patch (Vivelle®) were each applied centrally to circular specimens of complete human skin, measuring 4.52 cm$^2$. The skin samples thus prepared were placed for 72 h in modified Franz cells, there being no acceptor medium, so as to avoid artefacts as a result of back-diffusion into the cells. After the end of this time, the active substance patches were removed and the skin below the application site was punched out exactly. Further circular segments were punched out from the skin sample, each situated further and further from the core segment, that is, the actual release area of the TTS.

The skin samples obtained in this way were subsequently extracted with methanol for 16 h and assayed for residual estradiol. A horizontal concentration profile was found which was also statistically significant. The results of the residue assay are given in Table 1. The horizontal concentration profile found is reproduced in FIG. 4.

TABLE 1

| Skin segment | R1 | R2 | R3 | R4 |
| --- | --- | --- | --- | --- |
| Residual content in µg/cm$^2$ | 8.62 | 5.16 | 0.23 | 0.06 |

Key:
R1 = skin segment directly below the TTS application area (=1.13 cm$^2$)
R2 = 1st skin segment outside the TTS core segment (=1.41 cm$^2$)
R3 = 2nd skin segment outside the TTS core segment (=1.98 cm$^2$)
R4 = 3rd skin segment outside the TTS core segment (=2.54 cm$^2$)

EXAMPLE 2

An in vivo animal experiment was performed on two groups of rats each containing n=6 animals. Each of the animals from both groups had adhered to it a TTS containing a poorly absorbable active substance (morphine base). In the animals of the first experimental group, a cover patch containing an effective amount of a component which brings about a local temperature increase of the skin (ABC patches from Beiersdorf, Hamburg (DE)) was applied over the actual active substance release TTS. The effective substances of said cover patch are capsaicin and arnica extract. The areal skin contact of the cover patch in comparison to that of the active substance release TTS was 3 to 1.

The animals of the second experimental group (the control group) received as cover patch a self-adhesive occlusive film without a component which brings about a local temperature increase of the skin (Opraflex from Lohmann, Neuwied (DE)). The areal skin contact of the cover patch in comparison to that of the active substance release TTS was likewise 3 to 1.

After the end of the 24-hour period of wear, the patch dressings were removed and were assayed for residues of morphine base. The results are summarized in Table 2 and show that the use of a cover patch containing an effective amount of a component which brings about a local temperature increase of the skin increased the transdermal absorption rate from 5.7 to 26.4%.

TABLE 2

Experimental group with Opraflex cover patch

| TTS | Initial amount | Residue | Released |
|---|---|---|---|
| Verum 1 | 546.7 µg/cm² | 506.6 µg/cm² | 40.1 µg/cm² |
| Verum 2 | 546.7 µg/cm² | 514.2 µg/cm² | 32.5 µg/cm² |
| Verum 3 | 546.7 µg/cm² | 538.8 µg/cm² | 7.9 µg/cm² |
| Verum 4 | 546.7 µg/cm² | 528.0 µg/cm² | 18.7 µg/cm² |
| Verum 5 | 546.7 µg/cm² | 494.9 µg/cm² | 51.8 µg/cm² |
| Verum 6 | 546.7 µg/cm² | 510.0 µg/cm² | 36.7 µg/cm² |
| Mean: | | 515.4 µg/cm² | 31.3 µg/cm² |

This gives a relative absorption rate of 5.72%.

Experimental group with ABC-Wärme-Pflaster N cover patch

| TTS | Initial amount | Residue | Released |
|---|---|---|---|
| Verum 1 | 546.7 µg/cm² | 364.7 µg/cm² | 182.0 µg/cm² |
| Verum 2 | 546.7 µg/cm² | 354.6 µg/cm² | 192.1 µg/cm² |
| Verum 3 | 546.7 µg/cm² | 442.9 µg/cm² | 103.8 µg/cm² |
| Verum 4 | 546.7 µg/cm² | 447.9 µg/cm² | 98.8 µg/cm² |
| Verum 5 | 546.7 µg/cm² | 446.8 µg/cm² | 99.9 µg/cm² |
| Verum 6 | 546.7 µg/cm² | 359.0 µg/cm² | 187.7 µg/cm² |
| Mean: | | 402.7 µg/cm² | 144.1 µg/cm² |

This gives a relative absorption rate of 26.4%.

This result is all the more surprising since this method of improving the permeation of a transdermally administerable active substance through the skin is neither a chemical nor another invasive process which permanently damages the skin. Therefore, there is no intervention in the structure of the skin, especially the epidermis, and so neither is there any need to activate the "self-repair" mechanism of the skin.

On the basis of a local temperature increase and/or circulation increase of the skin, therefore, the device and the method bring about an increase in the rate of penetration into the skin and/or an increase in the travel through the skin and/or an increase in the transdermal absorption rate of an active substance applied to the skin.

Embodiments of the invention are elucidated using FIGS. 1 to 4.

Figure 1:
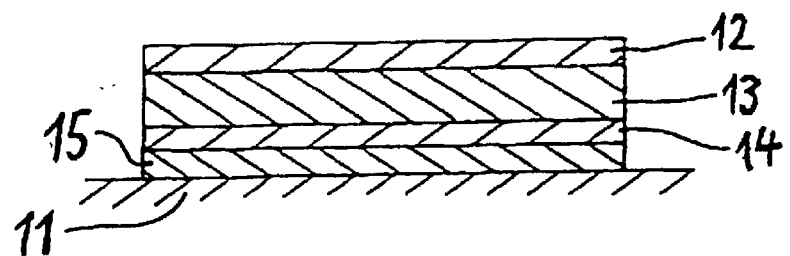
FIG. 1 shows an embodiment in which the component which brings about a local temperature increase and/or circulation increase in the skin is present in the same reservoir and in the same pressure sensitive adhesive layer as the active substance intended for transdermal administration. The reference symbols have the following meanings: 11=skin, 12=active substance impermeable backing layer, 13=reservoir containing the active substance intended for transdermal administration and, if appropriate, the component which brings about a local temperature increase and/or circulation increase in the skin, 14=semipermeable or microporous membrane for controlling active substance release, 15=pressure sensitive adhesive layer containing the active substance intended for transdermal administration and the component which brings about a local temperature increase and/or circulation increase in the skin.
Figure 2:
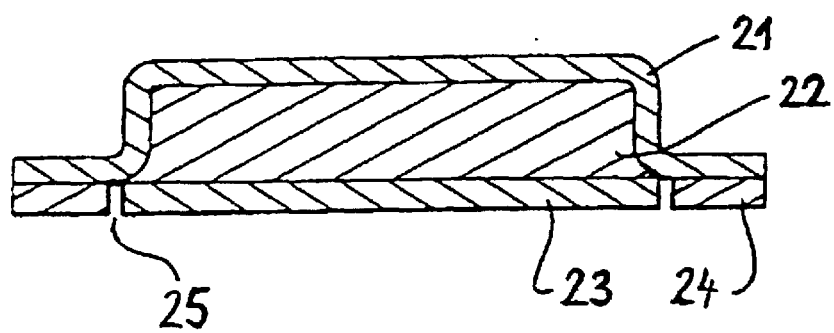
FIG. 2 shows an embodiment in which the component which brings about a local temperature increase and/or circulation increase in the skin is spatially separated by a vertical barrier layer from the reservoir and from the pressure sensitive adhesive layer containing the active substance intended for transdermal administration. The reference symbols have the following meanings: 21=active substance impermeable backing layer, 22=reservoir containing the active substance intended for transdermal application but free from the component which brings about a local temperature increase and/or circulation increase in the skin, 23=pressure sensitive adhesive layer containing the active substance intended for transdermal administration but free from the component which brings abouta local temperature increase and/or circulation increase in the skin, 24=pressure sensitive adhesive layer containing the component which brings about a local temperature increase and/or circulation increase in the skin, 25=vertical barrier layer.
Figure 3:
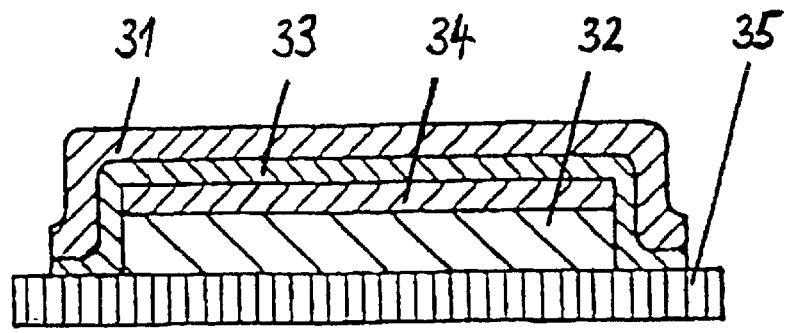
FIG. 3 shows an embodiment in which the component which brings about a local temperature increase and/or circulation increase in the skin is spatially separated by a horizontal barrier layer from the reservoir and from the pressure sensitive adhesive layer containing the active substance intended for transdermal administration. The reference symbols have the following meanings: 31=active substance impermeable backing layer, 32=reservoir or pressure sensitive adhesive layer containing the active substance intended for transdermal administration but free from the component which brings about a local temperature increase and/or circulation increase in the skin, 33=pressure sensitive adhesive layer containing the component which brings about a local temperature increase and/or circulation increase in the skin, 34=horizontal barrier layer, 35=skin.
Figure 4:
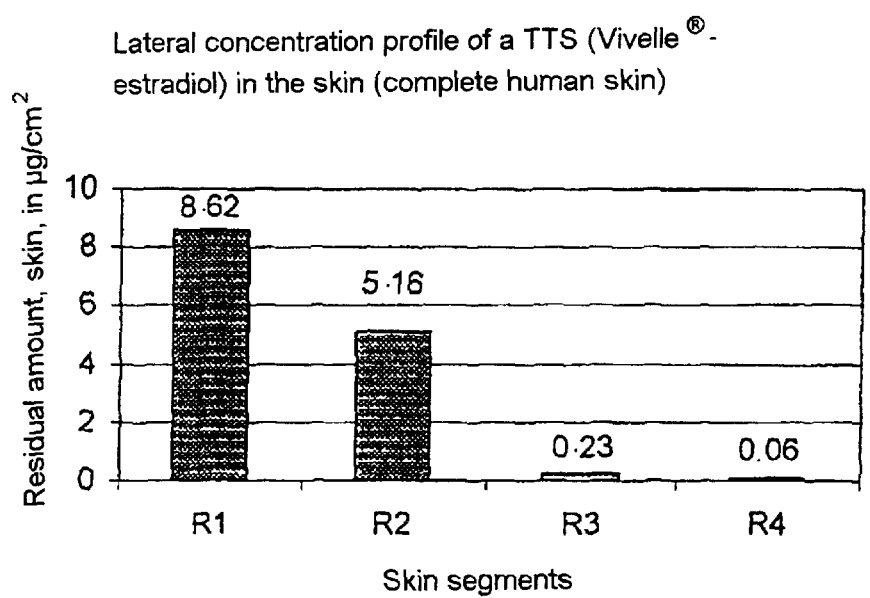
FIG. 4 depicts the horizontal concentration profile discussed in Example 1.

What is claimed is:

1. A device having a layered construction for transdermal administration of at least one active substance to a subject, said device comprising:

(a) a first layer comprising at least one active substance selected from the group consisting of pharmaceutically and cosmetically active substances, and (b) a second layer comprising at least one component that causes an increase in local temperature and/or blood circulation in the skin where said component is rubefacient which comprises pelargonic acid vanillyl amide, cayenne pepper oil resin, capsicum fruit extract, tincture of capsicum extract, cayenne pepper, or a combination of the foregoing, wherein the device contains an amount of said component effective to increase the rate of penetration of active substance(s) into the skin, the movement of active substance(s) through the skin and/or the transdermal absorption rate of said active substance(s) applied to the skin and wherein the first layer is spacially separated from the second layer.

2. The device as claimed in claim 1, which further comprises a backing layer that is impermeable to said component or that prevents emergence of said component on the side facing away from the skin.

3. The device as claimed in claim 1, which further comprises a pressure sensitive adhesive layer that extends over the full area of the bottom side of the device or that is located only- at the edge of the bottom side of the device.

4. The device as claimed in claim 1, wherein at least one horizontal barrier layer, at least one vertical barrier layer, at least one gap in the material and/or a mixture of the foregoing is used to separate spatially the first layer from the second layer.

5. The device as claimed in claim 1, wherein the pharmaceutically and/or cosmetically active substance possesses a systemic or topical action.

6. A method of enhancing the percutaneous permeation of a transdermally administrable active substance in a subject which comprises
   a) applying to a site of the skin in the subject a device comprising a component which causes an increase in temperature in blood and/or circulation in the local area of the site, thereby effecting a localized temperature increase in said site of the skin, and
   b) applying said active substance to said site of the skin, whereby said temperature increase in said site of the skin is sufficient to increase the rate of penetration of active substance(s), the movement of active substance(s) through the skin, and the transdermal absorption rate of active substance(s) applied to the skin.

7. The method according to claim 6, wherein the temperature increase is a short-term effect which lasts until the onset of the pharmacological effect of said active substance(s).

8. The method according to claim 6, whereas the temperature increase is a long-term effect throughout the duration of transdermal administration of said active substance(s).

9. The method according to claim 6, whereas the device comprising said component is selected from the group consisting of an ointment, a solution, a suspension, an emulsion, a foam, a paste, a gel or a patch.

10. The device as claimed in claim 1, wherein the pharmaceutically active substance is morphine, diamorphine, buprenorphine, fentanyl, 17β-estradiol, testosterone, norethisterone, or insulin.

11. The device according to claim 1, which does not comprise a permeation enhancer.

12. The device according to claim 1, which further comprises at least one additional permeation enhancer.

* * * * *